United States Patent [19]
Brohy et al.

[11] Patent Number: 5,480,386
[45] Date of Patent: Jan. 2, 1996

[54] PUMP ASSEMBLY FOR MEDICAL USE

[75] Inventors: Michael Brohy, Corseaux; Frédéric Neftel, Lausanne, both of Switzerland

[73] Assignee: Debiotech SA, Lausanne, Switzerland

[21] Appl. No.: 244,028

[22] PCT Filed: Sep. 14, 1993

[86] PCT No.: PCT/CH93/00222

§ 371 Date: Jul. 6, 1994

§ 102(e) Date: Jul. 6, 1994

[87] PCT Pub. No.: WO94/06491

PCT Pub. Date: Mar. 31, 1994

[30] Foreign Application Priority Data

Sep. 16, 1992 [CH] Switzerland ............... 2919/92

[51] Int. Cl.⁶ ................................. A61M 37/00
[52] U.S. Cl. ............... 604/131; 604/126; 604/151
[58] Field of Search .................... 604/123, 126, 604/131, 151, 890.1, 891.1, 905, 152, 153; 128/DIG. 12

[56] References Cited

U.S. PATENT DOCUMENTS

| | | |
|---|---|---|
| 4,360,019 | 11/1982 | Portner et al. ............. 604/131 |
| 4,487,603 | 12/1984 | Harris .................. 604/891.1 |
| 4,684,365 | 8/1987 | Reinicke . | |
| 4,685,902 | 8/1987 | Edwards et al. . | |
| 4,758,225 | 7/1988 | Cox et al. .............. 604/126 |
| 5,266,013 | 11/1993 | Aubert et al. ........... 604/153 |

FOREIGN PATENT DOCUMENTS

| | | |
|---|---|---|
| 0111723 | 6/1984 | European Pat. Off. . |
| 0142866 | 5/1985 | European Pat. Off. ....... 604/131 |
| 0433485 | 6/1991 | European Pat. Off. . |
| 0447909 | 9/1991 | European Pat. Off. . |
| 2644853 | 9/1990 | France . |
| 1077157 | 7/1967 | United Kingdom . |

Primary Examiner—C. Fred Rosenbaum
Assistant Examiner—Frank Wilkens, III
Attorney, Agent, or Firm—Young & Thompson

[57] ABSTRACT

A portable pump assembly for medical uses, and more particularly a portable micropump designed for the parenteral administration of medicamentous solutions includes a first module (2) provided with a container (8) designed for cooperating with a second motor module (4), the functioning of the pump being ensured by the assembling of the two modules. The first module (2) is provided with a removable filtering and sterilizing device (3), fastened to the filling septum orifice (10) of the container and including a filtering sterile plug (25) and a needle (28) surrounded by a flexible sleeve (29). A support arm (33) includes a guiding part (34) for guiding the device (3) when piercing the septum and an anchoring casing (40) closing the housing (39) for the second module (4). The first module (2) with the device (3) is provided in a sterile sealed pouch. The assembly is very easy to use, and aseptic conditions are guaranteed during the filling of the container (8).

11 Claims, 4 Drawing Sheets

PUMP ASSEMBLY FOR MEDICAL USE

FIELD OF THE INVENTION

The invention relates to a pump assembly for medical use, more specifically a portable pump or even micropump, designed for the patenreval ministration of medicamentous solutions.

BACKGROUND OF THE INVENTION

Since several years already, various types of pumps or micropumps for medical use are known. The so-called portable micropumps are particularly appreciated in the therapeutic treatment of patients such as those suffering from diabetes or cancer, who must receive permanently, or at least during extended periods of time, a controlled dose of a medicamentous substance administered continuously. The so-called peristaltic pumps or micropumps have been developed for such a use and are described in the specialized literature.

The patent application FR-A-89 04044 describes such a type of micropump. The same includes two separate modules, the so-called "motor" module which cannot be sterilized and which includes the motor and its control circuitry and the so-called "pump" module itself which can be sterilized and which includes a rotor provided with rollers, a tube and a pressing device cooperating with the rollers for pressing flat said tube. These two modules are assembled in a reversible manner.

The patent application EP-A 447 909 describes a model of a similar micropump, of which one main feature is the irreversible assembling of a "container" module and of a "motor" module. This micropump model further includes various safety systems which assist in ensuring asepsis during administration of the medicamentous solution to the patient, as well as in preventing any operating error by the patient himself. As illustrated in EP-A 0 447 909, the module including the container intended for the medicamentous solution has as a characteristic feature of the micropump, a filling orifice accessible to the user when the two modules are separated, but which is thereafter inaccessible to said user when said modules are assembled irreversibly. Subsequent access to the medicamentous solution is thus totally prevented, as well as any later contamination of this solution after it has been filled in a sterile manner into the storage container and this during the whole period of functioning of the micropump.

Although practice shows that this type of safety fulfils perfectly well its role once the micropump is in operation, the problem still remains of maintaining asepsis during the extemporaneous filling of the "container" module. The filling of such a module poses no real problem in a hospital environment, where trained staff and appropriate installations are available, such as for example a laminar flow hood or clean room; however, the filling by the patient himself, who cannot be expected to have the skill required, is another matter when a complete asepsis must be maintained during this operation and any accidental contamination of the medicamentous solution must be avoided. The invention provides a solution, which is new, original and technically reliable, to the problem described above.

SUMMARY OF THE INVENTION

Accordingly, an object of the invention is more particularly a portable pump assembly for the parenteral administration of medicamentous solutions including a first module provided with a storage container for the medicamentous solution, an orifice for filling said container and an outlet orifice for taking said medicamentous solution outside the pump, said first module being arranged to cooperate with a second module provided with a motor and with pumping means, the operation of the pump being ensured by the assembling of said first and second modules, said assembly being characterized in that the filling orifice of the storage container is provided with a removable filtering and sterilizing device.

In one particular embodiment of the invention, said pump can be of very small dimensions and weigh only a few grams, or at the most, several tens of grams. In such a case, the pump will more generally be referred to as being a "micropump"; a micropump according to the invention is particularly well suited for a variety of ambulatory treatments of patients.

According to the invention, the filtering and sterilizing device is an external device, i.e. is located fastened on the outer face of the filling orifice. Once the filling completed, it can easily be removed from the first module before assembling the same with the second module.

In a particular embodiment of the invention, the filling orifice of the container is of the septum type and the filtering and sterilizing device consists of a removable sterile filtering plug including on the one hand an adapter and on the other hand a needle extending through the septum. The removal of the filtering device after usage obviously implies also that of the needle. In another embodiment of the invention, the filling orifice is of the nonreturn valve type and the removable filtering and sterilizing device consists of a sterile filtering plug including on the one hand an adapter and on the other hand, a fluid-tight assembling means with the nonreturn valve. In such a case, only the sterile filtering plug with its adapter is removed after usage. Appropriate fluid-tight assembling means are available commercially.

According to the invention, the first module and the sterilizing and filtering device described above are made of a material which can withstand sterilization by means of ethylene oxide or of ionizing radiations, such as gamma rays. Such materials are mostly polymeric and are well known in the art.

Another object of the invention is a pump assembly for the parenteral administration of medicamentous solutions including a first module and a second module such as defined above, in which said first module with the removable filtering and sterilizing device is provided separate from the second module, in a sealed pouch made of a material which can be sterilized by means of ethylene oxide and/or by ionizing radiations.

The use of one particular embodiment of the invention can be described briefly as follows: the sterile pouch enclosing the "container" module provided with the removable filtering and sterilizing device is first opened with caution. A standard syringe containing the medicamentous solution, but without any needle is immediately connected to the adapter located upstream of the filtering plug. The medicamentous solution is then transferred into the storage container under the pressure exerted by the plunger of the syringe, through the filtering plug, after having moved the assembly in such a manner as to pierce the septum. Once the transfer of the solution has been completed by the user and while maintaining the syringe connected to the adapter, he removes delicately the device from its site, withdrawing at the same time the needle traversing the septum. Immediately after, the user connects the "motor" module to the "container" module, and the pump is ready to function.

In a preferred embodiment, the removable filtering and sterilizing device has a support member including a first part mounted removably on the first module and a second part designed for holding in place the removable filtering and sterilizing device. This construction confers a high level of safety and facilitates the use of the assembly.

Advantageously, the support element has a support arm provided with said first part consisting of an anchoring casing constructed in such a manner that it may be introduced in a housing of the first module and said second part consisting of a guide part designed for ensuring an axial sliding motion of the removable filtering and sterilising device.

It is also particularly advantageous that the support element includes a cover designed for closing the opening of said housing and that the removable sterilizing and filtering device includes a resilient protective sleeve connecting the support of the needle to an adapter of the filling orifice. This arrangement ensures an improved asepsis of the assembly.

Preferably, the pumping means are of the peristaltic type including flexible tubes positioned in said housing of the first module, the anchoring casing including at least one member designed for holding the tubes in their position, Thus, even under conditions of transport which may be difficult, an appropriate pumping is provided.

According to an advantageous embodiment, the support element has a housing into which at least the needle of the removable filtering and sterilizing device can be placed after the filling of the container. The needle is then carefully and rapidly wrapped up before being discarded.

The great usefulness of the support element should be stressed, since this single element fulfills at least five important functions, namely the support of the removable sterilizing and filtering device for facilitating the filling of the container, the axial guiding of this device during the perforation of the septum, the filling and the closing of the housing intended for the second motor module, the holding in position of the flexible tubes of the pump before its use and finally the wrapping up of the needle after use for its safe discarding.

Other advantages will appear from the characteristic features set forth in the appended claims and from the following detailed description of the invention made with reference to drawings which illustrate schematically and by way of example an embodiment of the invention and an alternate version thereof.

A BRIEF DESCRIPTION OF THE DRAWINGS

FIGS. 1a an 1b show the assembly before its use.

A DETAILED DESCRIPTION OF THE PREFERRED EMBODIMENT

Figure 1B:
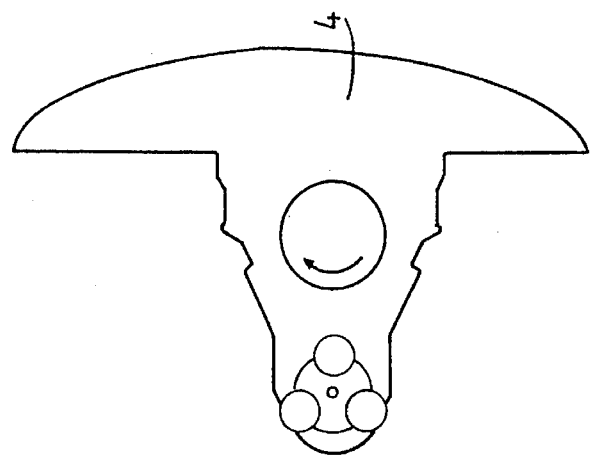
Figure 1A:
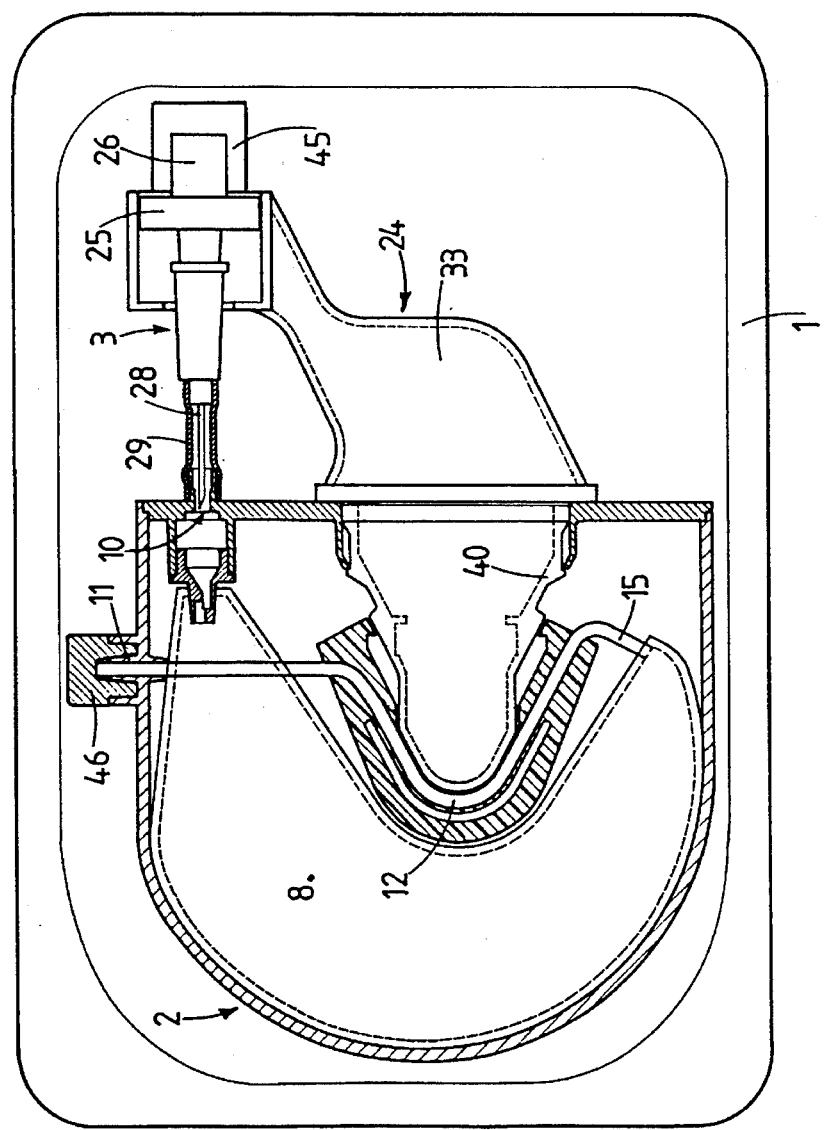

Referring to FIGS. 1a and 1b, the assembly is shown before its use in a sealed pouch 1 providing a sterile protection which is fluid-tight and which contains a first module 2 with its removable filtering and sterilizing device 3. The second module 4 comprised of a motor is provided separately. The first module 2 and its wrapping are wholly made of materials which can be sterilized, either by means of ethylene oxide or by means of ionizing radiations such as gamma rays, while the second module 4 is in principle not to be sterilized.

Figure 2:
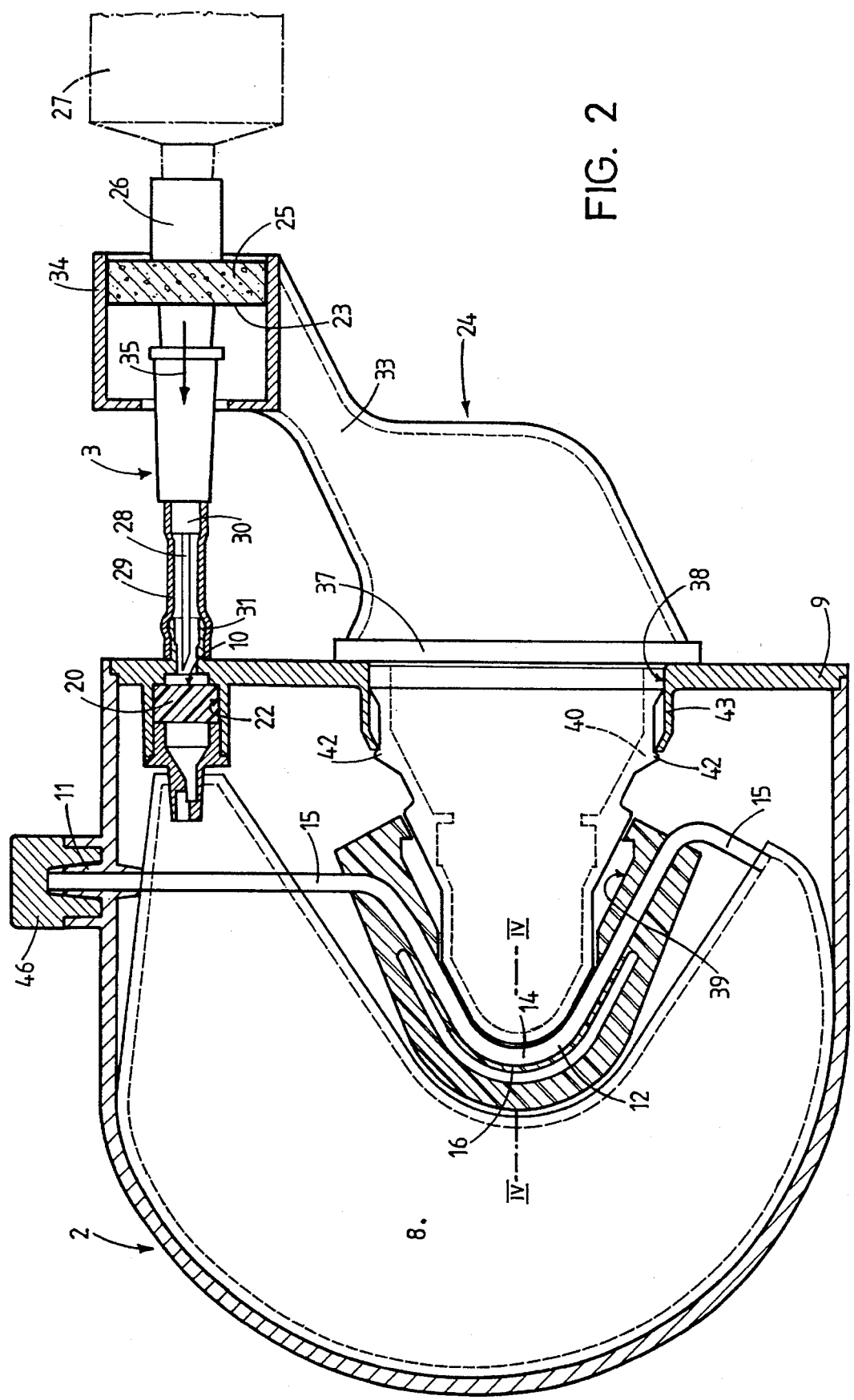
FIG. 2 illustrates the first module during the filling of the container.

Before the administration of the medicamentous solution, it is necessary to fill the storage container 8 of the first module 2. This module is illustrated in more detail in FIG. 2 and includes an outer wall 9 enclosing the container 8 connected to a filling orifice 10 and an outlet orifice 11. A conduit 15 which is part of a peristaltic pump brings the medicamentous solution from the container 8 to the outlet orifice 11. This conduit 15 is divided into two separate tubes 12, 13 (see FIG. 4) in its median part 14 where these separate tubes 12, 13 on the one hand press against a pump support 16 and on the other hand cooperate with rollers of the second motor module 4, when this second module 4 is mounted on the first module 2, in such a manner as to form the peristaltic pump, which is incidentally described in more detail in the application EP-A-0.447.909.

The filling orifice 10 is preferably constructed as a septum 20 including an elastomeric plug contained in a housing 22. The removable filtering and sterilizing device 3 itself is fastened to the external face of the filling orifice 10 and consists of a support element 24, of a conventional filtering sterile plug 25 having a pore size of 0,22 microns for example, contained inside a housing 23 having a standard medical adapter 26 for connecting to a conventional syringe 27, of a conventional medical needle 28 and of a resilient protective sleeve 29 bonded to the needle support 30 and firmly adapted to the adapter 31 of the orifice 10.

The support element 24 is of a complicated shape and has a first part comprised of a support arm 33 provided at one of its end with a guiding part 34 designed for ensuring the sliding motion of the housing 23 along an axial direction 35.

At its other end, the support arm includes a cover 37 designed for closing the opening 38 of the housing 39 into which the second module 4 is to be introduced for the administration of the medicamentous solution. The support arm 33 with its cover 37 continues as a casing 40 having a shape similar to that of the second module 4. This casing 40 is introduced into the housing 39 and is retained by protrusions 42 cooperating with flexible blades 43 made integral with the walls 9 of the first module 2. Thus, the casing 40 provides a stable anchoring means for the support element 24 on the first module 2. As shown in FIG. 1, the adapter 26 and the outlet orifice 11 are provided with stoppers 45, 46 closing the first module 2. These stoppers will be made fluid-tight or not depending on the method of sterilization retained, i.e. by means of ionizing radiations or of ethylene oxide.

When one wishes to use the assembly, the sterile pouch 1 is opened with care and the stoppers 45, 46 are removed from the adapter 26 and the outlet orifice 11. A catheter 52 is connected to the outlet orifice 11 and a standard syringe containing the medicamentous solutions, but without any needle, is connected immediately to the adapter 26 placed upstream of the filtering plug 25. The syringe 27, the filtering plug 25 and the needle 28 are then moved axially leftwards on FIG. 2 in such a manner that needle 28 penetrates through septum 20. When the needle support 30 comes in contact with the adapter 31, the septum 20 is traversed completely and the medicamentous solution can be transferred into the container 8 through the filtering plug 25 under the pressure exerted by the piston of the syringe. The support element 24 with its guiding part 34 confers a high stability to the assembly and ensures the proper sliding of the filtering plug 25 and of the needle upon its introduction, during which the resilient protective sleeve 29 is compressed.

Figure 3:
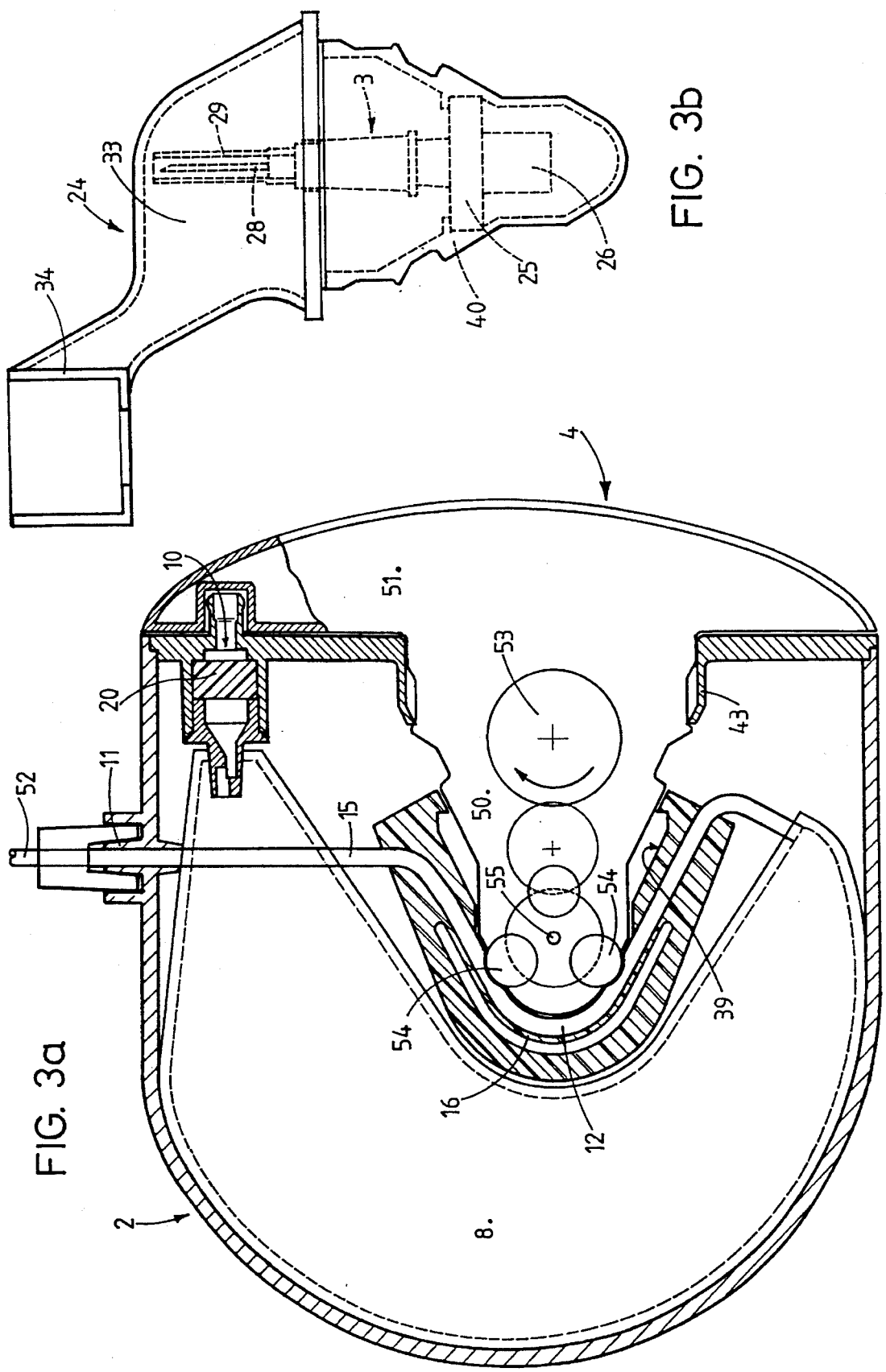
FIGS. 3a and 3b show the assembly during the administration of the medicamentous solution.

FIGS. 3a and 3b illustrate the situation after the filling of the container 8. Once the transfer of the medicamentous solution is completed, the user, while maintaining the syringe 28 connected to the adapter 26, removes the totality of the support element 24 with the casing 40, against the biasing force of the flexible blades 43. This removal obviously brings about that of the needle 28 and of the protective sleeve 29 by the baring of the adapter 31. The user then connects immediately the second motor module 4 to the first module 2, by introducing its second protruding part 50 into the housing 39. The outer part 51 of this second module 4 is constructed in such a manner as to close completely the filling orifice 10 and to guarantee the proper asepsis of the assembly. Once the catheter 52 is connected to the outlet orifice 11, the medicamentous solution is administered at the desired flow rate to the patient.

To this end, the motor 53 contained in the second module 4 drives through gears a rotor provided with rollers 54 to rotate around the axis 55. These rollers 54 cooperate with flexible separate tubes 12 and 13 for providing a pump of the peristaltic type.

It will then be possible to remove the syringe 27 from the adapter 26. The assembly formed of the filtering plug 25, the needle 28 and the sleeve 29 will then be removed from the guiding part 34 and placed inside the casing 40 and the support arm 33 which has for this purpose a face which is open or partly open. The support element 24 hence provides both means for holding in position the removable filtering and sterilizing device 3 during the filling of the container 8 and means for protecting the needle to be discarded.

Figure 4:
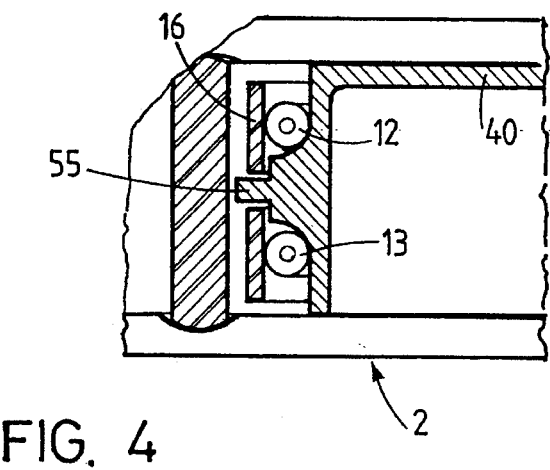
FIG. 4 is a detailed cross-sectional view according to IV—IV of FIG. 2.

FIG. 4 shows that the support element with its casing 40 has a third important function, namely that of holding the two flexible separate tubes 12, 13 of the peristaltic pump before the introduction of the second motor module 4. Actually, the two separate tubes 12, 13 could move laterally during transport inside the first module and thus prevent a proper functioning of the peristaltic pump during the administration of the medicamentous solution. To prevent such undesirable displacements, the casing 40 is provided in its front part with at least one protrusion 55 designed for holding the separate tubes 12, 13 in position, when the support element 24 is mounted on the first module 2.

Figure 5:
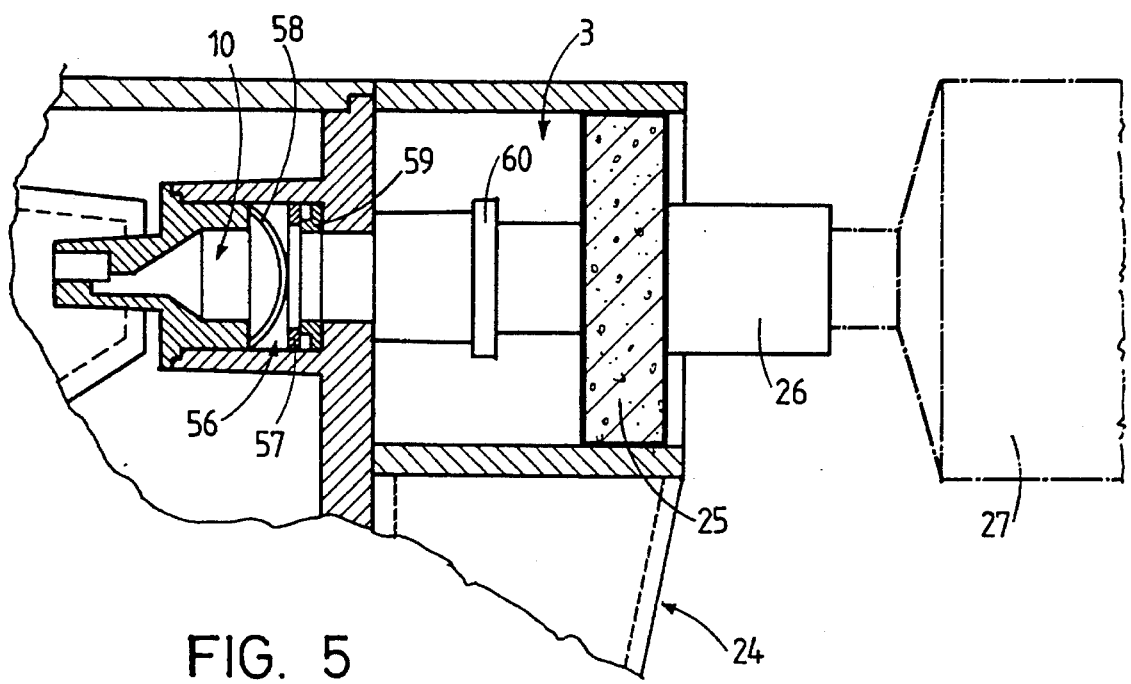
FIG. 5 is a detailed view of another version.

According to an alternate version illustrated in FIG. 5, the filling orifice 10, instead of having a septum, is provided with a nonreturn valve 56. The latter has a valving member 57 biased resiliently by the resilient blades 58 against a seat 59. The support element 24 maintains releasably as described previously a filtering sterile plug 25 including on the one hand an adapter 26 for a syringe 27 and on the other hand a fluid-tight assembling member 60 with the nonreturn valve 56. It is obvious that the filtering plug 25 is maintained here rigidly without sliding by the support element 24.

The first module 2 and the sterilizing and filtering devices described above are made from material capable of withstanding sterilization by means of ethylene oxide and/or ionizing radiations such as gamma rays. Such materials, predominantly polymeric materials, are well known to those skilled in the art. The construction of the assembly makes it possible to make pumps of a very small size, i.e. micropumps.

Obviously, the embodiments described above do not limit in any manner the invention and can undergo any desirable modification within the framework defined in the claims. In particular, the pump may be made differently or may be of another type. More or less sophisticated control means can be associated with the pump, which make possible a controlled administration of medicaments in the course of time and/or which is for example regulated by measured physiological parameters. The construction and the components of the support and of the container may be made differently, and also the support arm 33 can be of a similar form to that of the outer part 51 of the second motor module 4.

We claim:

1. An assembly forming a portable pump for the parenteral administration of medicamentous solutions, comprising a first module including a storage container for the medicamentous solution, an inlet means for filling said container, an outlet means for delivering said medicamentous solution outside the pump, and a second module having a motor and pumping means, said first module constructed and arranged to cooperate with the second module, said pumping means adapted to operate by the assembling of said first and second module, and said inlet means including a removable sterilizing filter device having readily detachable connection means for connecting and disconnecting the sterilizing filter device to an external face of said inlet means.

2. An assembly according to claim 1, further comprising means for making the inlet means inaccessible to a user by the assembling of the first and the second modules once said removable sterilizing filter device is removed from an initial position after filling the storage container.

3. An assembly according to claim 1, wherein the first module is provided separately from the second module, in a fluid-tight pouch made of a material adapted to be sterilized by at least one of ethylene oxide and ionizing radiations.

4. An assembly according to claim 1, wherein the inlet means includes a non-return valve and the removable sterilizing filter device includes a sterile filtering plug having an adapter and a fluid-tight assembling member with the non-return valve.

5. An assembly according to claim 1, wherein the first module and the removable sterilizing filter device are made of components adapted to be sterilized by at least one of ethylene oxide and ionizing radiations.

6. An assembly according to claim 1, wherein the inlet means includes a septum, and the removable sterilizing filter device includes a sterile filtering plug having an adapter and a needle for piercing the septum.

7. An assembly according to claim 6, wherein the removable sterilizing filter device has a support element including a first part removably mounted on the first module and a second part for maintaining in place the removable sterilizing filter device.

8. An assembly according to claim 7, wherein the support element has a support arm provided with said first part comprising an anchoring casing constructed and arranged for introduction into a housing of the first module, and with said second part comprising a guiding for ensuring an axial sliding motion of the removable sterilizing filter device.

9. An assembly according to claim 8, wherein the support element includes a cover for closing an opening of said housing, and the removable sterilizing filter device includes a resilient protective sleeve connecting a support of the needle to an adapter of the inlet means.

10. An assembly according to claim 8, wherein the pumping means comprise a peristaltic pump including flexible tubes positioned in said housing of the first module, and said anchoring casing includes at least one member for holding the tubes in place.

11. An assembly according to claim 7, wherein the support element has a housing for storing the needle of the removable sterilizing filter device after filling the container.

* * * * *